United States Patent
Schein et al.

(10) Patent No.: US 6,476,253 B1
(45) Date of Patent: Nov. 5, 2002

(54) PROCESS FOR PREPARING MONOACETYLATED HYDROQUINONE COMPOUNDS

(75) Inventors: Karin Schein, Ludwigshafen; Kai-Uwe Baldenius, Frankenthal; Wolfgang Siegel, Limburgerhof; Rainer Stürmer, Rödersheim-Gronau; Detlef Ruff; Hagen Jaedicke, both of Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/677,860

(22) Filed: Oct. 3, 2000

(30) Foreign Application Priority Data

Oct. 20, 1999 (DE) .......................................... 199 50 616

(51) Int. Cl.⁷ ............................................... C07C 67/00
(52) U.S. Cl. ..................... 560/131; 568/319; 568/322; 568/323
(58) Field of Search .......................... 560/131; 568/319, 568/322, 323

(56) References Cited

U.S. PATENT DOCUMENTS 3,377,241 A  4/1968  Broadbent et al.

FOREIGN PATENT DOCUMENTS

FR  2 655 335  6/1991

OTHER PUBLICATIONS

Cohen N et al J. Org. Chem (1979) 44(22) 4005–7 Chem Abst. 91:193242.*
Cohen et al. "Fries Rearrangement of Trimethylhydroquinone Diacetate. A Novel Hydroquinone to Resorcinol Transformation" J. Org. Chem. vol. 43 (1978) pp. 3723–3726.
Lee et al. "Syntheses of Flavones from Lindrea lucida" J. Chem. Soc. (1965) pp. 2743–2749.
Höfle et al. "Stigmaellin A und B—zwei neue Antibiotika aus *Stigmatella aurantiaca*(Myxobacterales)" Liegigs Ann. Chem. (1984) pp. 1183–1904.

* cited by examiner

Primary Examiner—Paul J. Killos
(74) Attorney, Agent, or Firm—Keil & Weinkauf

(57) ABSTRACT

The present invention relates to a process for preparing monoacetylated hydroquinone compounds of the formula I,

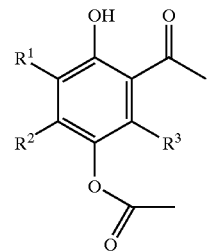

to the novel final products of the process and to a process for preparing the precursors.

8 Claims, No Drawings

PROCESS FOR PREPARING MONOACETYLATED HYDROQUINONE COMPOUNDS

The present invention relates to a process for preparing monoacetylated hydroquinone compounds and to the novel final products of the process.

Hydroquinone compounds are intermediates in demand for preparing natural substances, vitamins and carotenoids. For example 2,3,6-trimethylhydroquinone is used in the industrial total synthesis of α-tocopherol (vitamin E) (Ullmann's Encyclopedia of Industrial Chemistry, 5th edition, Vol. A27, pp. 484 et seq., 4.11.2).

To prepare vitamin E compounds with olefinic isoprenoid side chains such as tocotrienol, another synthetic route is necessary because the acidic synthesis conditions usual for preparing tocopherol lead to isomerization or cyclization of the olefinic side chain (P. Karrer, H. Reutschler, *Helv. Chim. Acta* 1944, 27, 20 1297; H. J. Kabbe, A. Widdig, *Angew. Chem. Int. Ed. Engl.* 1982, 21, 247–256, P. Schudel, H. Mayer, J. Metzger, R. Rüegg, O. Isler, *Helv. Chim. Acta* 1963, 46, 2517).

Tocotrienols as well as tocopherols can be synthesized, for example, by reacting dihydroxyacetophenone compounds and E,E-farnesylacetone under basic conditions to give the corresponding 4-oxotocotrienols (H. J. Kabbe et al., *Angew. Chem. Int. Ed. Engl.* 1982, 21, 247–256; B. C. Pearce et al., *J. Med. Chem.* 1994, 37, 526) and subsequently reducing the 4-oxotocotrienols to the tocotrienols (H. J. Kabbe, H. Heitzer, *Synthesis* 1978, 888; B. C. Pearce et al., *J. Med. Chem.* 1994, 37, 526–541).

Monoacetylated hydroquinone compounds which can be converted into the corresponding dihydroxyacetophenone compounds by hydrolysis with, for example, methanolic sodium hydroxide (N. Cohen et al, *J. Org. Chem* 1978, 43 (19), 3723–3726) are therefore intermediates in particularly great demand.

It is known to prepare 2-acetyl-3,5,6-trimethylhydroquinone which is monoacetylated on the position 4 oxygen from 2,3,6-trimethylhydroquinone by reaction with BF$_3$/acetic acid (N. Cohen et al, *J. Org. Chem* 1978, 43 (19), 3723–3726).

This process has the disadvantage that the precursors employed are themselves hydroquinones which have to be prepared from low-cost precursors such as phenols by an elaborate process with at least two synthesis steps (Ullmann's Encyclopedia of Industrial Chemistry, 5th edition, Vol. A27, p. 485, 4.11.3).

It is an object of the present invention to remedy the described deficiencies and to provide a novel process for preparing monoacetylated hydroquinone compounds with advantageous properties.

We have found that this object is achieved by a process for preparing monoacetylated hydroquinone compounds of the formula I

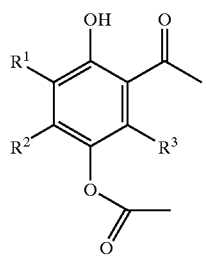

I where

R$^1$, R$^2$ or R$^3$ is, independently of one another, hydrogen or methyl, which comprises reacting diacetylphenol compounds of the formula

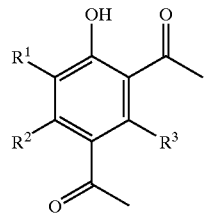

II with peroxo compounds, where appropriate in the presence of an acid.

It was not to be expected that oxidation of asymmetrically acetylated phenols can be carried out with high selectivity in relation to an acetyl group in high yields.

Höfle et al. describe the monooxidation of a symmetrically diacylated dimethoxyphenol by means of a Baeyer-Villiger oxidation (Liebigs Ann. Chem. 1984, 1883–1904).

It is moreover known from another class of substances that re action of 3, 5-diacetyl-1,2,4-trimethoxybenzene with peracetic acid provides 5-acetoxy-3acetyl-1,2,4-trimethoxybenzene as byproduct in 30% yield (H.H. Lee et al., J. Chem. Soc. 1965, 2743–2749).

Peroxo compounds mean according to the invention inorganic or organic compounds comprising a peroxide group. Examples of preferred peroxo compounds are H$_2$O$_2$ or peracids or salts thereof.

H$_2$O$_2$ can be employed in the process according to the invention for example as aqueous solution.

Examples of preferred peracids are inorganic peracids or optionally substituted percarboxylic acids such as, for example, optionally substituted aryl peracids or optionally substituted C$_1$–C$_4$-alkyl peracids.

Examples of suitable substituents for the aforementioned percarboxylic acids are NO$_2$ or halogen.

Preference is given to optionally halogenated percarboxylic acids such as, for example, optionally halogenated aryl peracids or optionally halogenated C$_1$–C$_4$-alkyl peracids.

Halogenated percarboxylic acids mean percarboxylic acids which may be substituted by up to 6 identical or different halogen radicals such as, for example, F, Cl, Br or I, preferably F or Cl.

In a preferred embodiment of the process, the optionally substituted percarboxylic acids can be prepared in situ using H$_2$O$_2$ and the corresponding optionally substituted carboxylic acid.

Examples of preferred optionally halogenated C$_1$–C$_4$-alkyl peracids are performic acid, peracetic acid, trifluoroperacetic acid or monopermaleic acid.

Examples of preferred optionally substituted aryl peracids are perbenzoic acid, m-chloroperbenzoic acid, 3,5-dinitroperbenzoic acid, p-nitroperbenzoic acid, monoperphthalic acid.

Suitable and preferred salts of the optionally substituted percarboxylic acids are their alkali metal or alkaline earth metal salts such as, for example, the magnesium salt of monoperphthalic acid.

Examples of preferred inorganic peracids or salts thereof are peroxosulfuric acids such as H$_2$S$_2$O$_8$ or H$_2$SO$_5$ or alkali metal or alkaline earth metal salts thereof, such as, for example, K$_2$S$_2$O$_8$, or peroxophosphoric acids such as H$_4$P$_2$O$_8$ or H$_3$PO$_5$ or sodium perborates such as, for example, NaBO$_3$.

Suitable and particularly preferred peroxo compounds in the process according to the invention are H$_2$O$_2$ or m-chloroperbenzoic acid.

The diacetylphenol compounds of the formula II are reacted in the process according to the invention with peroxo compounds in the presence or absence of an acid.

The process according to the invention for preparing monoacetylated hydroquinone compounds of the formula I can in principle be carried out with peroxo compounds in the absence of an acid.

The process according to the invention for preparing monoacetylated hydroquinone compounds of the formula I can advantageously be carried out in a preferred embodiment in the absence of an acid specifically on use of peracids such as, for example, performic acid, peracetic acid, trifluoroperacetic acid, monopermaleic acid, perbenzoic acid, m-chloroperbenzoic acid, 3,5-dinitroperbenzoic acid, p-nitroperbenzoic acid, monoperphthalic acid, $H_2S_2O_8$, $H_2SO_5$, $H_4P_2O_8$ or $H_3PO_5$ as peroxo compounds.

The process can preferably and particularly advantageously be carried out when the diacetylphenol compounds of the formula II are reacted with peroxo compounds in the presence of an acid.

An acid means according to the invention a Brönsted or Lewis acid, a mixture of Brönsted acids, a mixture of Lewis acids or a mixture of Brönsted and Lewis acids.

Preferred Brönsted acids are inorganic acids such as, for example, $H_2SO_4$ or HCl or carboxylic acids, in particular optionally halogenated carboxylic acids, such as optionally halogenated $C_1$–$C_4$-alkylcarboxylic acids, such as, for example, formic acid, acetic acid, propionic acid or trifluoroacetic acid.

Preferred Lewis acids are the halides of main group three, such as, for example, $BF_3$ or $AlCl_3$.

Preferred acids are formic acid and trifluoroacetic acid.

In a particularly preferred embodiment of the process, the following combinations of peroxo compounds and acids are used:

$H_2O_2$ and formic acid,
$H_2O_2$ and $H_2SO_4$,
$H_2O_2$ and $BF_3$,
m-chloroperbenzoic acid and trifluoroacetic acid,
$K_2S_2O_8$ and $H_2SO_4$,
$NaBO_3$ and trifluoroacetic acid or
$NaBO_3$ and trifluoroacetic acid/acetic acid.

The process according to the invention can advantageously be carried out with the addition of a buffer system such as, for example, an $Na_2HPO_4$ buffer.

The process for preparing the compounds of the formula I can be carried out without additional solvent or in inert organic solvents such as, for example, $CH_2Cl_2$ or $CHCl_3$.

In the case where the process for preparing the compounds of the formula I is carried out without additional solvent, the acid may act as solvent. The acid is employed in excess in this case. The amount of added acid is not critical and is typically, depending on the dilution, 30 to 60 mol eq., based on the compound of the formula II to be reacted.

In the case where the process for preparing the compounds of the formula I is carried out in the absence of acid, the inert organic solvent acts as solvent.

It may moreover be advantageous to carry out the process for preparing the compounds of the formula I in an inert organic solvent and in the presence of an acid. In this case, the amount of added acid is likewise not critical and is typically 0.001 mol eq. to 4 mol eq., in particular 0.01 mol eq. to 2 mol eq., based on the compound of the formula II to be reacted.

The stoichiometric amounts of the peroxo compounds employed are not critical and are typically 1 to 10 mol eq., in particular 2 to 4 mol eq., based on the compound of the formula II to be reacted.

The process temperature is not critical and is typically −80° C. to 100° C., in particular 0° C. to 30° C.

The product of the formula I of the process can be isolated by methods known per se, for example by extraction, chromatography or destillation methods.

It may in this connection be advantageous to add, before the isolation and after the cessation of reaction, peroxo scavengers such as, for example, $Na_2S_2O_3$ while cooling in ice in order to destroy excess peroxo compounds.

The monoacetylated hydroquinone compounds of the formula I preferably prepared in the process according to the invention are those where $R^1=R^2=R^3$=methyl or
$R^1=R^3$=methyl, $R^2$=hydrogen or
$R^1=R^2$=methyl, $R^3$=hydrogen or
$R^1$=methyl, $R^2=R^3$=hydrogen.

The present invention also relates to a process for preparing diacetylphenol compounds of the formula II

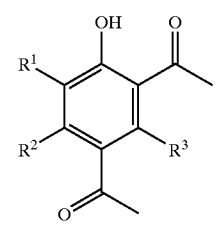

II where
$R^1$, $R^2$ or $R^3$ is, independently of one another, hydrogen or methyl, which comprises reacting phenol compounds of the formula III

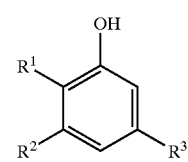

III with an acetylating agent in the presence of an acidic catalyst.

It is known to prepare diacetylphenol compounds of the formula II for $R^1$ and $R^2$=methyl and $R^3$=hydrogen by a two-stage process from the corresponding phenol compound of the formula III (H.-J. Knölker et al., Helv. Chim. Acta 1993, 76, 2500–2514). This is done by acetylating, in the first step, the free hydroxyl group of 2,3-dimethylphenol with acetic anhydride and added base. In a second step, the resulting O-acetyl compound is converted by Fries rearrangement into 2,4-diacetyl-5,6-dimethylphenol in yields of less than 10%.

The process has the disadvantage that it takes place by two separate steps and affords the required product only as byproduct in yields of less than 10%.

It was surprising that carrying out the process with an acetylating agent in the presence of an acidic catalyst, that is to say in one step, affords the required product in higher yields.

An acetylating agent means compounds able to transfer an acetyl group.

Examples of preferred acetylating agents are acetic acid, acetyl halides, in particular acetyl chloride, acetic anhydride or other active esters of acetic acid, in particular acetic acid N-hydroxysuccinimide ester or phenol esters and halophenol esters of acetic acid.

A particularly preferred acetylating agent is acetyl chloride.

An acidic catalyst means Brönsted acids, preferably HF, $H_2SO_4$, $H_3PO_4$ or $HClO_4$ or Lewis acids, preferably $AlCl_3$, $BF_3$, $FeCl_3$, $TiCl_4$, $ZnCl_2$, $SbF_5$ or $SbCl_5$.

In a preferred embodiment of the process for preparing compounds of the formula II, an acetyl halide, in particular acetyl chloride, is used as acetylating agent, and a Lewis acid, in particular $AlCl_3$, is used as acidic catalyst.

The stoichiometric amounts of the reagents employed are not critical and are typically 1 to 20 mol eq., in particular 4 to 10 mol eq., of the acidic catalyst and 1 mol eq. to 20 mol eq., in particular 2 mol eq. to 8 mol eq., of the acetylating agent, in each case based on the compound of the formula III to be reacted.

Solvents suitable for the process for preparing diacetylphenol compounds of the formula II are conventional organic solvents, in particular optionally substituted hydrocarbons, such as, for example, dichloromethane, 1,2-dichloroethane, nitrobenzene, trichloroethylene or $CHCl_3$.

The temperature during the process for preparing diacetylphenol compounds of the formula II is not critical and is typically –20° C. to 100° C. Depending on the precursor and the temperature chosen, the time until conversion ceases in the reaction is from 1 to 20 h.

In a preferred embodiment, the process for preparing compounds of the formula II is carried out in an inverse reaction. This entails introduction of the acetylating agent and the Lewis acid into a solvent, and dropwise addition of the compound of the formula III. The dropwise addition is advantageously controlled so that the reaction temperature does not exceed 20° C.

The product of the formula II of the process can be isolated by methods known per se, such as extraction, chromatography or distillation methods. It may be advantageous in this connection to add water to quench the reaction mixture before the isolation.

The present invention also relates to an overall process for preparing monoacetylated hydroquinone compounds of the formula I

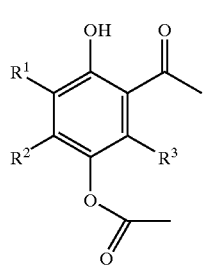

by reacting phenol compounds of the formula III

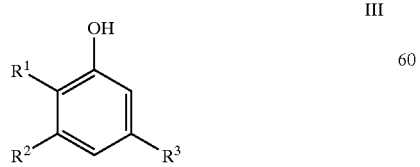

with an acetylating agent in the presence of an acidic catalyst to give the diacetylphenol compounds of the formula II

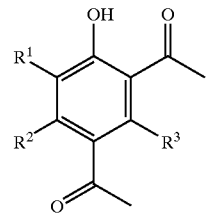

and reacting the latter with peroxo compounds, where appropriate in the presence of an acid.

The overall process can be carried out in one step or in two steps with isolation of the intermediates of the formula II. The process is preferably carried out in two steps.

The invention also relates to compounds of the formula Ia to Ie,

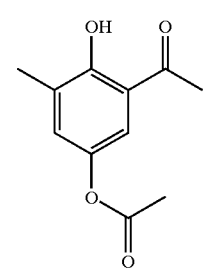

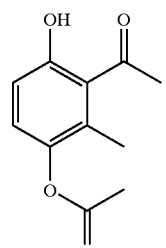

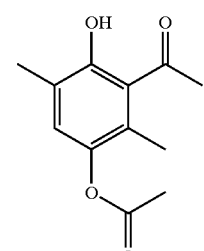

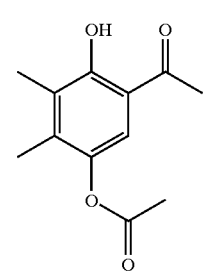

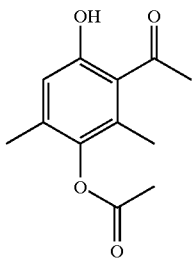

The following examples illustrate the invention:

EXAMPLE 1

Preparation of Compounds of the Formula II Using Acetyl Chloride and $AlCl_3$ 0.6 mol of aluminum trichloride was introduced into 240 ml of 1,2-dichloroethane, and 0.5 mol of acetyl chloride was added at temperatures equal to or less than 200° C. Then 0.1 mol of the compound of the formula III (dissolved in 50 ml of 1,2-dichloroethane) was added dropwise while cooling in ice so that 20° C. was not exceeded. The mixture was then heated to reflux.

After 5–13 h, the reaction was cooled and quenched with water while cooling in ice. The phases were separated, the aqueous phase was extracted 3 times with 200 ml of methyl t-butyl ether each time, and the combined organic phases were washed with saturated $NaHCO_3$ solution until the aqueous phase remained alkaline. After washing with saturated NaCl solution and drying over $MgSO_4$, the solvent was removed in a rotary evaporator, and the residue underwent column chromatography (silica gel 60 (230 to 400 mesh); eluent: heptane/ethyl acetate).

The above experiment was carried out with 2,3-dimethylphenol (Example 1.1) and 2-methylphenol (Example 1.2) as compound of the formula III.

EXAMPLE 1.1

Preparation of 2,4-Diacetyl-5,6-dimethylphenol (IId)

Reaction of 2,3-dimethylphenol by the general method described in Example 1 afforded 2,4-diacetyl-5,6-dimethylphenol (IId) in 66% yield (after column chromatography) with a conversion of 100%;

GC-MS: 206; $^1$H-NMR($CDCl_3$, 400 MHz) in [ppm]: 2.19 (s, 3H); 2.43 (s, 3H); 2.64 (s, 3H); 7.91 (s, 1H); 13.0 (s, 1H); $^{13}$C-NMR($CDCl_3$, 100 MHZ) in [ppm]: 11.16; 18.01; 26.35; 29.67; 115.90; 127.45; 129.64; 130.40; 145.92; 162.54; 200.45; 203.98.

EXAMPLE 1.2

Preparation of 2,4-Diacetyl-6-methylphenol (IIa)

Reaction of 2-methylphenol by the general method described in Example 1 afforded 2,4-diacetyl-6-methylphenol (IIa) in 27% yield (after column chromatography) with a conversion of 100%;

GC-MS: 192; $^1$H-NMR:($CDCl_3$, 400 MHz) in [ppm]: 2.28 (s, 3H); 2.58 (s, 3H); 2.71(s, 3H); 7.91(s, 1H); 8.23 (s, 1H); 13.0 (s, 1H); $^{13}$C-NMR:($CDCl_3$, 100 MHz) in [ppm]: 15.54; 26.24; 26.76; 118.33; 127.82; 127.86; 129.61; 136.61; 164.67; 196.03; 205.02;

EXAMPLE 2

Preparation of Compounds of the Formula I Using Formic Acid and $H_2O_2$ 10 mmol of $H_2O_2$ (30% by volume in $H_2O$) were added to 5 mmol of the compound of the formula II and 0.20 mol of formic acid over the course of 5 minutes. The mixture was then stirred at room temperature for 8 h. Then, while cooling in ice, $Na_2S_2O_3$ was added and, after dilution with 50 ml of $H_2O$, extraction was carried out with 3×25 ml of toluene. The combined organic phases were adjusted to pH=6 with triethylamine, washed with water and dried over $MgSO_4$, and the solvent was removed in a rotary evaporator. The yield was determined via the GC percentage area of the crude product.

The above experiment was carried out with 2,4-diacetyl-5,6-dimethylphenol (IId) (Example 2.1) and 2,4-diacetyl-6-methylphenol (IIa) (Example 2.2) as compound of the formula II.

EXAMPLE 2.1

Preparation of 2-Acetyl-4-acetoxy–5,6-dimethylphenol (Id)

Reaction of 2,4-diacetyl-5,6-dimethylphenol (IId) by the general method described in Example 2 afforded 2-acetyl-4-acetoxy–5,6-dimethylphenol (Id) in 96% yield with a conversion of 97%;

$^1$H-NMR($CDCl_3$, 400 MHz) in [ppm]: 2.12 (s, 3H); 2.19 (s, 3H); 2.32 (s, 3H); 2.58 (s, 3H); 7.228 (s, 1H); 12.5 (s, 1H). $^{13}$C-NMR($CDCl_3$, 100 MHz) in [ppm]: 11.35; 13.71; 20.72; 26.52; 116.68; 120.05; 127.22; 158.43; 169.82; 203.69.

EXAMPLE 2.2

Preparation of 2-Acetyl-4-acetoxy–6-methylphenol (Ia)

Reaction of 2,4-diacetyl-6-methylphenol (IIa) by the general method described in Example 1 afforded 2-acetyl-4-acetoxy–6-methylphenol (Ia) in 87% yield with a conversion of 98%;

GC-MS: 208; $^1$H-NMR($CDCl_3$, 400 MHz) in [ppm] : 2.26 (s, 3H); 2.30 (s, 3H); 2.60 (s, 3H) 7.09 (s, 1H); 7.30 (s, 1H); 12.40 (s, 1H); $^{13}$C-NMR($CDCl_3$, 100 MHz) in [ppm]: 15.58; 20.97; 26.75; 118.45; 199.99; 129.02; 130.74; 141.35; 158.72; 169.87; 204.08;

EXAMPLE 3

Preparation of Compounds of the Formula I Using Trifluoroacetic acid and m-Chloroperbenzoic acid in Dichloromethane 5 mmol of the compound of the formula II were dissolved in 60 ml of dichloromethane and, while cooling in ice, firstly 15 mmol of m-chloroperbenzoic acid and then, dropwise, 5 mmol of trifluoroacetic acid were added. After the addition, the ice bath was removed and the mixture was stirred at room temperature for 8 h. After completion of the reaction, the excess reagent was destroyed with $Na_2S_2O_3$, and the reaction mixture was washed with 25 ml each of saturated aqueous $NaHSO_3$ solution, saturated aqueous $NaHCO_3$ solution and water and dried over $MgSO_4$. After removal of the solvent, the crude yield was determined.

The above experiment was carried out with 2,4-diacetyl-5,6-dimethylphenol (IId) (Example 3.1) as compound of the formula II.

EXAMPLE 3.1

Preparation of 2-acetyl-4-acetoxy-5,6-dimethylphenol (Id)

Reaction of 2,4-diacetyl-5,6-dimethylphenol (IId) by the general method described in Example 3 afforded 2-acetyl-4-acetoxy-5,6-dimethylphenol (Id) in 85% crude yield; $^{1}$H-NMR(CDCl$_{3}$, 400 MHz) in [ppm]: 2.12 (s, 3H); 2.19 (s, 3H); 2.32 (s, 3H); 2.58 (s, 3H); 7.228 (s, 1H); 12.5 (s, 1H). $^{13}$C-NMR(CDCl$_{3}$, 100 MHz) in [ppm]: 11.35; 13.71; 20.72; 26.52; 116.68; 120.05; 127.22; 158.43; 169.82; 203.69.

We claim:

1. A process for preparing monoacetylated hydroquinone compounds of the formula I

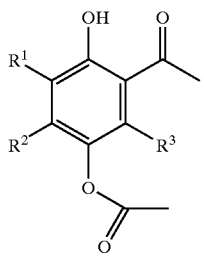

where $R^{1}$, $R^{2}$ and $R^{3}$ are, independently of one another, hydrogen or methyl, which comprises reacting diacetylphenol compounds of the formula II

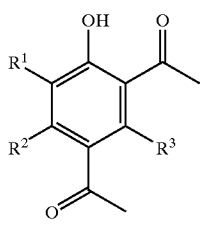

with peroxo compounds, where appropriate in the presence of an acid.

2. A process as claimed in claim 1, wherein the diacetylphenol compounds of the formula II are reacted with peroxo compounds in the presence of an acid.

3. A process as claimed in claim 2, wherein H$_{2}$O$_{2}$ or peracids or salts thereof are used as peroxo compounds.

4. A process as claimed in claim 2, wherein an optionally halogenated carboxylic acid is used as acid.

5. A process for preparing diacetylphenol compounds of the formula II

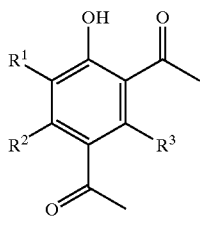

where $R^{1}$, $R^{2}$ and $R^{3}$ are, independently of one another, hydrogen or methyl, which comprises reacting phenol compounds of the formula III

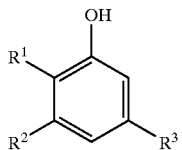

with an acetylating agent in the presence of an acidic catalyst.

6. A process as claimed in claim 5, wherein acetic acid, acetyl halide or acetic anhydride is used as acetylating agent.

7. A process for preparing monoacetylated hydroquinone compounds of the formula I

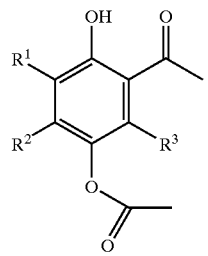

where $R^{1}$, $R^{2}$ and $R^{3}$ are, independently of one another, hydrogen or methyl, which comprises reacting phenol compounds of the formula III

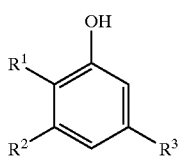

with an acetylating agent in the presence of an acidic catalyst to give the diacetylphenol compounds of the formula II

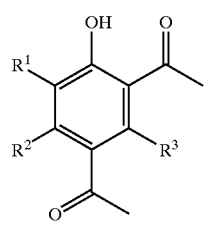

and reacting the latter with peroxo compounds, where appropriate in the presence of an acid.

8. A compound of the formula Ia, Ib, Ic, or Id
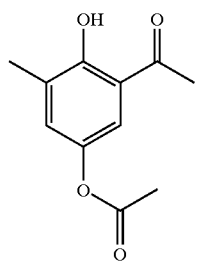
Ia
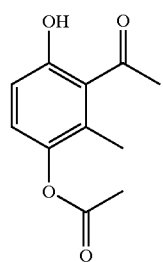
Ib
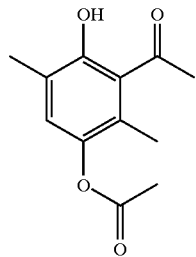
Ic
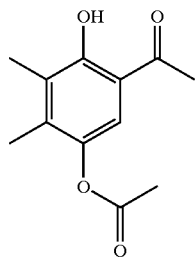
Id
* * * * *